United States Patent [19]

Claes et al.

[11] Patent Number: 4,557,743
[45] Date of Patent: Dec. 10, 1985

[54] METHOD OF AND APPARATUS FOR MONITORING THE REDOX STATE OF ELEMENTS IN GLASS

[75] Inventors: Paul Claes, Court Saint Etienne; Christian Dauby, Gerpinnes; Camille Dupont, Heppignies; Luc Van Cangh, Pont à Celles, all of Belgium

[73] Assignee: Glaverbel, Brussels, Belgium

[21] Appl. No.: 646,443

[22] Filed: Aug. 31, 1984

[30] Foreign Application Priority Data

Sep. 1, 1983 [GB] United Kingdom ............... 8323519

[51] Int. Cl.⁴ .............................................. C03B 5/16
[52] U.S. Cl. .......................................... 65/29; 65/32; 65/134; 65/157; 65/161
[58] Field of Search .................... 65/29, 32, 157, 161, 65/134

[56] References Cited

U.S. PATENT DOCUMENTS

| 3,295,944 | 1/1967 | Baak | 65/29 |
| 3,298,872 | 1/1967 | Baak | 65/29 X |
| 3,854,919 | 12/1974 | Pirooz | 65/134 X |
| 4,358,305 | 11/1982 | Sleighter | 65/161 X |

FOREIGN PATENT DOCUMENTS

| 0203397 | 10/1983 | German Democratic Rep. | 65/29 |
| 709826 | 6/1954 | United Kingdom | |
| 820244 | 9/1959 | United Kingdom | |
| 1401761 | 7/1975 | United Kingdom | |
| 1412545 | 11/1975 | United Kingdom | 65/134 |
| 1539393 | 1/1979 | United Kingdom | |

OTHER PUBLICATIONS

T. R. Copeland et al., 'Anodic Stripping Voltammetry', Analytical Chemistry, vol. 46, No. 14, Dec. 1974.
Jud B. Flato, 'The Renaissance in Polarographic and Voltammetric Analysis', Analytical Chemistry, vol. 44, No. 11, Sep. 1972.
E. Plumat et al., "Formation of Bubbles by Electrochemical Processes in Glass", Oct. 1966, Journal of the American Ceramic Society, vol. 49, No. 10, pp. 551–558.

*Primary Examiner*—Arthur Kellogg
*Attorney, Agent, or Firm*—Spencer & Frank

[57] ABSTRACT

A method of and apparatus for monitoring the redox state of one or more elements in glass are disclosed in which a working electrode 2 and an auxiliary electrode 7 are immersed in the glass 11 while the latter is molten. A scanning potential is applied to the working electrode, a series of potential pulses is superimposed on said scanning potential, and the resulting current between the electrodes is monitored to give an indication of the redox state of one or more elements in the glass.

22 Claims, 13 Drawing Figures

U.S. Patent  Dec. 10, 1985  Sheet 1 of 4  4,557,743
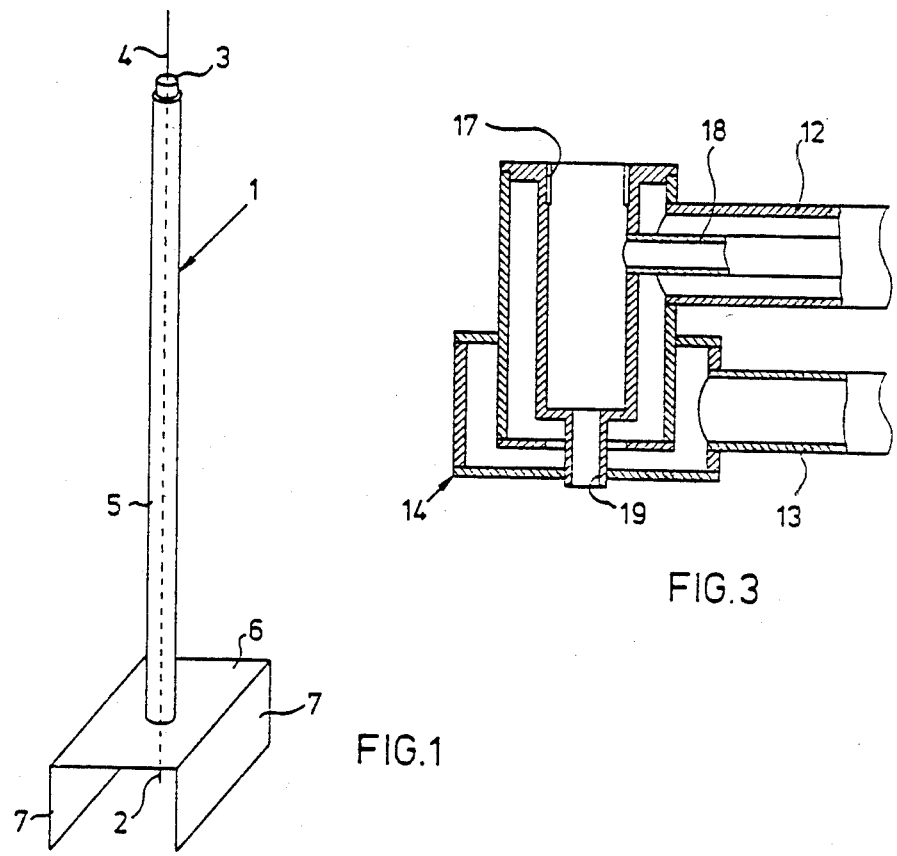
FIG.1
FIG.3
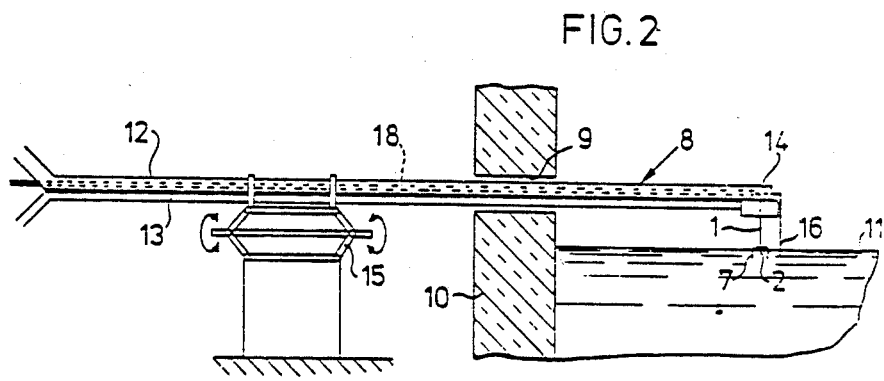
FIG.2

METHOD OF AND APPARATUS FOR MONITORING THE REDOX STATE OF ELEMENTS IN GLASS

BACKGROUND OF THE INVENTION

This invention relates to a method of and apparatus for monitoring the redox state of elements in glass.

The redox state of variable valency elements in glass is governed by the conditions under which the glass is formed, the principal determining factors being the composition of the atmosphere under which the glass is melted and the composition of the batch. Thus the redox state of such elements is governed by the fuel/air mixture feeding the flames of a glass melting furnace, and by the quantities of oxidising agents such as sodium sulphate and of reducing agents such as sulphides, coke and metallic ions which may be incorporated into the batch feeding the furnace. Other factors also have an effect on the redox state of elements in the glass, and among these factors may be cited the temperatures to which the molten glass is subjected during manufacture, and the time for which the glass is subjected to such temperatures. The redox state can thus vary with the rate of glass output from the furnace, whether this can be a gas-fired furnace or an electric furnace or a furnace which is heated by both gas and electricity. The redox state can also vary with the state of the checker-worker in a regenerator furnace, and thus with the age of the furnace.

The redox state of variable valency elements in glass can have an important effect on the properties, particularly the radiation transmitting properties, of the glass produced. By way of example, the following may be cited:

Iron. Iron is present in almost all commercially produced glass. either as an impurity, or as a deliberately introduced colouring agent. The presence of $Fe^{3+}$ ions in glass gives rise to slight absorption of short-wavelength visible light and to a very strong absorption band in the ultra-violet region, while the presence of $Fe^{2+}$ ions gives rise to strong absorption in the infrared. Thus, for example, if it is desired to produce a glass having a high energy transmission in respect of solar radiaton, the iron should be in the higher oxidation state. In addition, ferric iron imparts a mild yellow colouration to the glass, and ferrous iron a stronger greenish-blue colour.

Sulphur. Sulphur is also present in much commercially produced glass, having been introduced as sulphate, as a refining agent, or sulphide, as a melting accelerator. While sulphur in higher oxidation states has practically no colouring effect, the $S^{2-}$ anion, especially in the presence of iron, can give rise to a yellowish-brown colour.

In addition to iron and sulphur, glass often contains other colouring agents, whether introduced deliberately or present as impurities. Some of the more important colouring agents for glass are referred to below.

Selenium. The $Se^{4+}$ cation has practically no colouring effect, whereas the uncharged $Se^0$ element imparts a pink colouration. The $Se^{2-}$ anion forms a chromophore with any ferric ions present, and this gives a brownish red colour to glass.

Chromium. The presence of the coordinate $[Cr^{III}O_6]$ gives rise to absorption bands at 450 nm and 650 nm to give a clear green colour. Strong oxidation gives rise to the coordinate $[Cr^{VI}O_4]$ which gives a very intense absorption band at 365 nm giving a yellow colouration.

Manganese. $Mn^{2+}$ ions have practically no colouring effect, but $Mn^{3+}$ ions give rise to a violet colour.

Nickel. The group $[Ni^{II}O_4]$ gives rise to a blue colouration of the glass, and the group $[Ni^{II}O_6]$ to a yellow colouration.

The colouring effect of other agents such as cobalt, cerium, copper, titanium and vanadium is also dependent on their oxidation state.

The importance of monitoring the redox of the glass constituents in order to control the quality of the glass produced will therefore be appreciated.

Hitherto, the redox state of the glass constituents has been monitored in respect of the glass after it has been formed into the desired product, whether this be sheet glass or hollow ware. Such monitoring was effected indirectly by optical spectroscopy, X-ray fluorescence, and electronic paramagnetic resonance techniques. By way of example, for clear glass containing iron, the relative proportions of ferric and ferrous ions present was calculated from the transmissivity of the glass in respect of light having wavelengths of 380 nm and 1050 nm, and the total iron concentration was obtained by X-ray fluorescence.

SUMMARY OF THE INVENTION

It is an object of the present invention to give a more rapid indication of the redox state of the glass constituents so that any necessary corrective action may in turn be taken more rapidly.

According to the present invention, there is provided a method of monitoring the redox state of one or more elements in glass, characterised in that a working electrode and an auxiliary electrode are immersed in the glass while the latter is molten, in that a scanning potential is applied to the working electrode, a series of potential pulses is superimposed on said scanning potential, and in that the resulting current between the electrodes is monitored to give an indication of the redox state of one or more elements in the glass.

The present invention extends to apparatus for performing such a method, and accordingly provides apparatus for monitoring the redox state of elements in glass, characterised in that such apparatus comprises a working electrode and an auxiliary electrode suitable for immersion in molten glass, means for applying a scanning potential to said working electrode and for superimposing potential pulses on said scanning potential, and means for monitoring resulting current flow between the electrodes.

By operating in accordance with the present invention, a more rapid indication of the redox state of the glass constituents can be obtained, so that any necessary corrective action may in turn be taken more rapidly, than enabling a reduction in the production of glass of an undesired quality.

As the scanning potential applied to the working electrode varies, it is clear that the current in the molten glass between that working electrode and the other, auxiliary electrode will also vary. The current through the 'cell' formed by the two electrodes and the molten glass 'electrolyte' may notionally be split into three components: a first, continuous component which is due to the scanning potential applied at any given instant, and two intermittent components due to the superimposed pulses, namely a capacitive components which decays exponentially, and a faradic component which lasts for the duration of the pulse, and is inversely proportional to the square root of its duration.

Considering now the faradic current component in isolation, the current monitored will exhibit peaks in the course of time as the scanning potential varies. The scanning potential at which such a peak occurs will be characteristic of a particular electrochemical reaction, and thus of the redox state of a particular element in the glass. The height of such a peak will vary in direct proportion to the concentration in the glass of that particular element species, and in proportion to the square of the number of electrons transferred, while the width of the peak at half its height will be inversely proportional to the number of electrons transferred.

For example, at $-520$ mV scanning potential, there will be a current peak corresponding to a reversible redox reaction involving iron. Thus as the scanning potential difference increases (away from zero) through $-520$ mV, it is possible to obtain a direct indicating of the concentration of iron ions in the molten glass. From this information, and from the total iron concentration in the glass, the redox state of that iron is easily deducible. Of course if there is no iron present in the glass, there will be no such peak. The total iron concentration in the glass tends to remain substantially constant over periods lasting several days in industrial production, and is easily evaluated after the glass has been formed by classical methods such as X-ray fluorescence.

Throughout this specification, including the claims hereof, references to specific potentials, (and potential ranges,) are references to potentials measured with reference to a stabilized zirconia reference electrode as described in the article entitled "Formation of Bubbles by Electrochemical Processes in Glass" by, E. Plumat et al. appearing in *Journal of the American Ceramic Society* Vol. 49, No. 10, October 1966, Pages 551 to 588.

It will be appreciated that the redox state of a species such as iron will give an indication of the oxidising or reducing conditions under which the molten glass was formed, and from this a close estimation of the redox state of other species, for example sulphur, though not of the concentration, can be made. In order to obtain similar data in respect of such another species, it would be necessary to scan through the potential appropriate to that species.

The electrodes may be immersed in the molten glass at any convenient position in the glass melting furnace, but it is preferred that such monitiring is effected on molting glass having a temperature coresponding to a viscosity between $10^{5.2}$ and $10^{1.5}$ poises and preferably in the range between $10^{3.8}$ and $10^{2.8}$ poises. These viscosity values correspond, for soda-lime glass, to temperature ranges of 900° C. to 1630° C., and preferably 1150° C. to 1250° C. At such temperatures, the glass has a sufficiently low visosity for ease of monitoring, without being so hot as to involve great difficulty in fabricating electrodes able to withstand the heat during such monitoring.

It is preferred that said electrodes be of platinum or platinum alloy. Platinum electrodes are well able to withstand the corrosive effects of molten glass.

Preferably, said scanning potential varies linearly with time. This facilitates monitoring of the induced current, particularly monitoring of the intermittent faradic component in isolation. By way of example, in one practical embodiment of the invention, the scanning potential is varied at a constant rate of 20 mV/s.

Advantageously, when such monitoring is effected on soda-lime glass, said scanning potential scans over a range which includes one or more of the following potentials: $+120$ mV, O, $-105$mV, $-380$ mV, $-520$ mV, $-580$ mV, $-680$ mV, $-750$ mV.

Reactions have been found to take place in molten soda-lime glass at a temperature of 1200° C. at those potentials indicated in the following table when the potential is scanned in the direction away from zero.

| Potential | Reactive element | Probable Reaction |
|---|---|---|
| $+120$ mV | selenium | $Se^O - 4e^- <=> Se^{4+}$ |
| O | chromium | |
| $-105$ mV | selenium | $Se^{2-} - 2e^- <=> Se^O$ |
| $-380$ mV | sulphur | $S^{4+} + 4e^- <=> S^O$ (adsorbed) |
| $-520$ mV | iron | $Fe^{2+} + 2e^- <=> Fe^O$ |
| $-580$ mV | sulphur | $S^{4+} + 4e^- <=> S^O$ |
| $-680$ mV | sulphur | $S^{6+} + 6e^- -> S^O$ |
| $-750$ mV | chromium | |

Examination of the current peak at any of the potentials indicated will give an indication of the concentration of the given reactive element, provided that the scanning potential is scanning in the direction away from zero. The reactions involving iron at $-520$ mV, sulphur at $-380$ mV and $-580$ mV are reversible when scanning in the opposite direction (i.e. towards zero). When scanning towards zero potential, there are only two peaks involving sulphur.

Advantageously, said scanning potential scans over a range which includes the range 0 to $-800$ mV, and which most preferably includes one or both of the ranges 0 to $+500$ mV and 0 to $-100$ mV, and it is preferred that said scanning potential is caused to scan to and fro in positive- and negative-going directions. Scanning to and fro facilitates the separation of faradic component current density peaks due to different electrochemical reactions which take place during the course of monitoring.

In the most preferred embodiments of the invention, said superimposed pulses are uniform square wave pulses. This can readily be achieved by incorporating a square wave generator in the means for superimposing said potential pulses. The use of square wave pulses simplifies calculation of the concentration of the element species to whose presence any particular current peak is due.

Advantageously, the current monitored is the difference between the current flowing immediately before the end of a said pulse and the current flowing immediately before the start of that pulse. Provided that the rate of variation of the scanning potential is not too large, that the measured current is independent of the frequency of the pulses, and that the length of the pulse is sufficient for the induced capacitive current component to decay, the adoption of this feature allows a sufficiently accurate and direct reading of the intermittently induced faradic current component. In order to ensure that the measured current is independent of the frequency of the pulses, the pulse frequency is adjusted to be within a frequency range across which the current is found not to vary.

Preferably, the working electrode is located between plates constituted by the auxiliary electrode, and the electrodes are immersed in the glass so that such electrode plates define sides of a channel through which can flow natural or induced currents of molten glass. The adoption of this preferred feature has the advantage of substantially avoiding any effects within the direction or velocity of such glass currents might have on the intermittently induced electric current.

Preferably, said working electrode is of substantially circular cross section, and in the most preferred embodiments of the invention, said working electrode comprises a stem and an enlarged working portion for immersion in the glass. The adoption of this feature reduces the effect which undesired variations in the depth of immersion of the working electrode in the molten glass will have on the monitored current density. In fact the current between the electrodes will be proportional to the area immersed and inversely proportional to the resistance of the cell.

It is preferred that the means for monitoring current flow comprises a polarograph.

Preferably, said electrodes ar mounted on an arm which is constituted as a cooling jacket for connector leads. This helps protect such leads from the environment in the glass melting furnace.

The present invention includes a method of manufacturing glass wherein the batch composition and/or the fuel/air mixture fed to burners for melting the glass and/or injection of gas into the melt is or are adjusted in dependence on the redox state of one or more elements in the glass as monitored by a method as herein defined, in order to maintain or achieve a desired redox state of such element(s).

The invention is applicable to the manufacture of flat glass, for example float or drawn glass, to the manufacture of other glass products for example tubing and hollow ware such as bottles, and to the manufacture of clear or coloured glass.

BRIEF DESCRIPTION OF THE DRAWING

Preferred embodiments of the present invention will now be described by way of example only with reference to the accompanying diagrammatic drawings, in which:

FIG. 1 is a perspective view of an electrode assembly used in an apparatus according to the invention;

FIG. 2 is a sectional side view of a support for the electrode assembly used to implement the method of the invention;

FIG. 3 is a detail sectional view of the end of the electrode support;

DESCRIPTION OF THE PREFERRED EMBODIMENT

Figure 4:
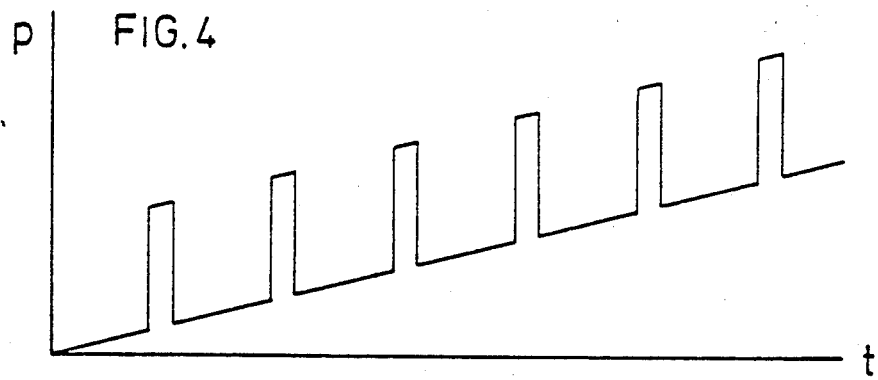
FIG. 4 is a graph showing potential applied to the electrode assembly of FIGS. 1 and 2 in accordance with the method of the invention.

In FIG. 1, an electrode assembly 1 comprises a first electrode 2 to which potential is to be applied and which projects from a refractory insulating tube 3. A connector lead 4 for that working electrode 2 leads through the insulating tube 3. A conductive sleeve 5 surrounds the insulating tube 3, and at its lower end carries an inverted square U-section channel member 6 whose side plates 7 constitute an auxiliary electrode.

In a specific practical embodiment, the working electrode 2 is constituted by a wire, 1 mm in diameter, made of platinum, and the insulating tube 3 is of alumina having internal and external diameters of 3 mm and 6 mm respectively. The conductive sleeve 5 is of a platinum-rhodium alloy, and has internal and external diameters of 6.6 mm and 7 mm respectively. The channel member 6 is of the same platinum-rhodium alloy, 1 mm thick, and is welded to the sleeve 5. The side plates 7 are each 35 mm long and 30 mm high, and they are spaced apart by 30 mm, with the working electrode 2 midway between them. The assembly is designed so that when the side plates 7 are each immersed in molten glass to a depth of 10 mm, the working electrode 2 is immersed to a depth of 5 mm.

FIG. 2 shows the electrode assembly 1 carried by a support 8 which projects through a hole 9 in the wall of a part of a glass melting furnace 10 so that the electrodes 2, 7 are immersed in molten glass 11. For example, electrodes may be immersed in glass in a distribution channel of a flat-glass melting furnace or in a feeder of a container-glass melting furnace. The support 8 comprises two parallel tubes 12, 13 joined by a head 14 from which the electrode assembly depends. The tubes 12, 13 are mounted one above the other and carried by a scissor jack assembly 15 for raising and lowering the support 8, so that electrodes 2, 7 of the assembly 1 can be withdrawn from the immersed into the molten glass 11, and so that the depth of their immersion can be varied. The head 14 also carries a thermocouple 16 for measuring the temperature of the molten glass close to the electrode assembly 1. The thermocouple 16 is suitably a platinum and platinum/ (10%) rhodium thermocouple.

The head 14 of the support 8 is shown in greater detail in FIG. 3. In use, a cooling fluid, such as water, enters the head 14 through the lower support tube 13, and circulates around a central chamber 17 to leave the head 14 through the upper support tube 12. The upper support tube 12 contains a conduit 18 for connector leads (not shown in FIG. 3) for the electrode assembly 1 and thermocouple 16 (FIG. 2). The electrode assembly would project downwardly from an aperture 19 at the base of the central head chamber 17.

FIG. 4 is a graph illustrating a potential which may be applied to the working electrode 2 of FIGS. 1 and 2, and shows a potential which scans at a uniform rate, for example, varying at 20 mV/s on which pulses, shown as a series of uniform, square wave pulses, are superimposed. Such pulses may have an amplitude of 10 mV, a duration of 88 ms and a frequency of 2.5 Hz.

Figure 5A:
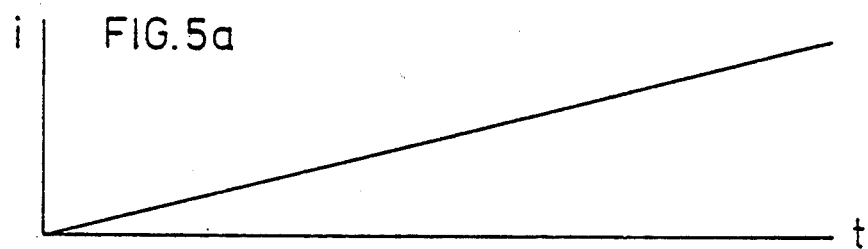
FIGS. 5a, 5b and 5c comprise graphs illustrating resulting current components induced between the electrodes of FIGS. 1 and 2.
Figure 5B:
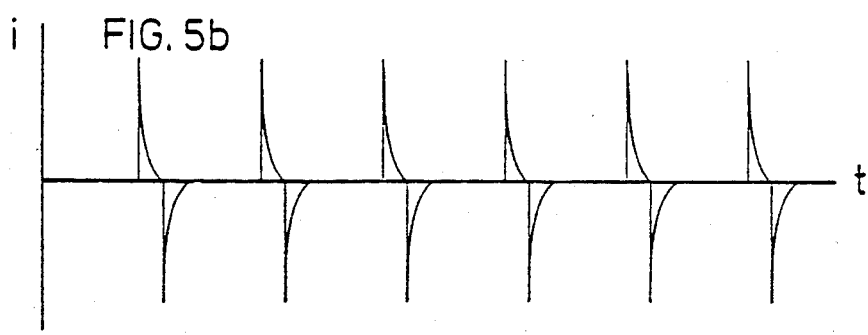
Figure 5C:
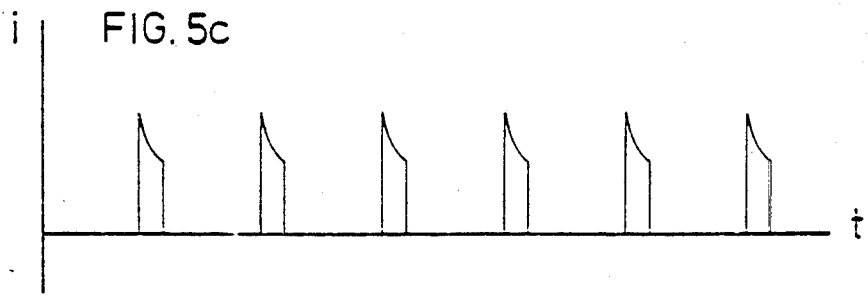

FIG. 5a illustrates the resulting current component which is due to the basic scanning potential, FIG. 5b illustrates a capacitive current component due to charging and discharging of the condenser formed around the working electrode, and FIG. 5c illustrates a faradic current component due to electrochemical reactions initiated and maintained by the potential pulses. A direct indication of the faradic current component is obtained by differencing the currents flowing immediately before the beginning and immediately before the end of each potential pulse.

The current flowing in the cell formed by the electrodes and the molten glass will vary in proportion to the immersed electrodes area but differences in the depths of immersions of the electrodes can be compensated for if the resistance of the cell is monitored. It is extremely surprising that the rate of flow of the molten glass past the electrodes appears to have no effect on the results obtained.

Figure 6:
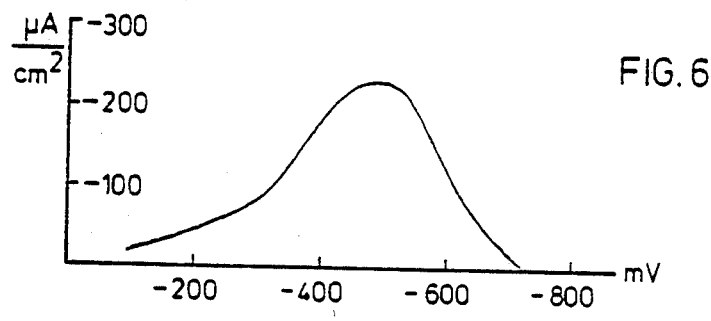
FIGS. 6 to 10 show graphical plots of the currents induced in glasses of various different compositions at different applied potentials in an application of the method according to the invention.
Figure 7:
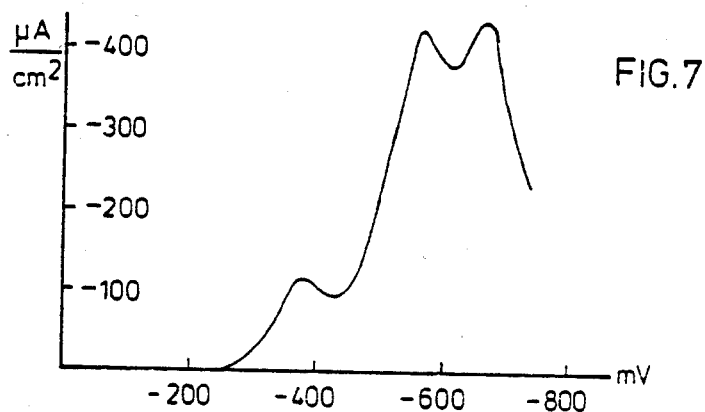
Figure 8:
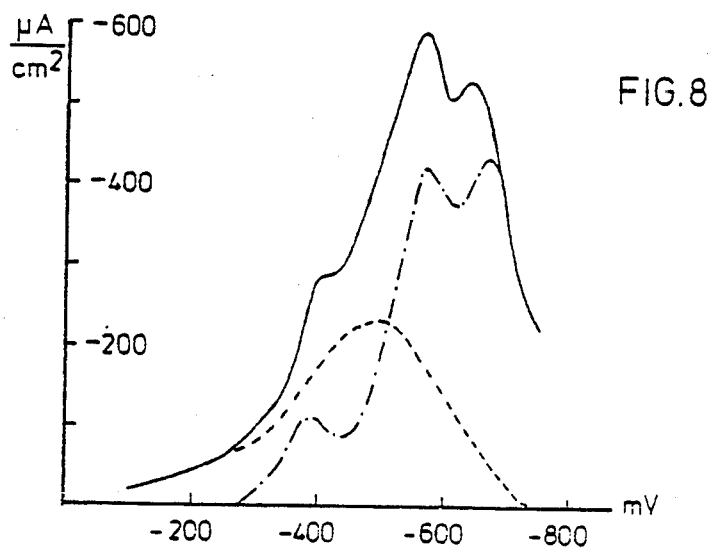

FIGS. 6, 7, and 8 show graphical representation of monitored faradic components of current density against applied potential in ordinary clear soda-lime glass at a temperature of 1200° C.

In FIG. 6, which was obtained by scanning from 0V to −800 mV in a low-sulphur, iron-containing glass, there is a current density peak at −520 mV which corresponds to the reduction of iron ions. The height of this peak is directly proportional to the concentration of iron ions in the molten glass, and corresponds to a total iron content in the glass of 0.384% by weight calculated as ferric oxide. In fact sulphur content of the glass calculted as $SO_3$ was 0.022% by weight.

FIG. 7 shows a similar graph drawn in respect of a low-iron, sulphur-containing glass, and it will be noted that there are current density peaks at −380 mV and −580 mV corresponding to the presence of sulphur in the state $S^{4+}$. The height of the peak at −580 mV is proportional to the concentration of that species, but the height of the peak at −380 mV is only proportional to the concentration of that species for low sulphur concentrations. This glass had an iron content of 0.076% and a sulphur content of 0.322%, both calculated as before.

FIG. 8 shows a similar graph drawn in respect of a glass containing iron and sulphur.

Figure 9:
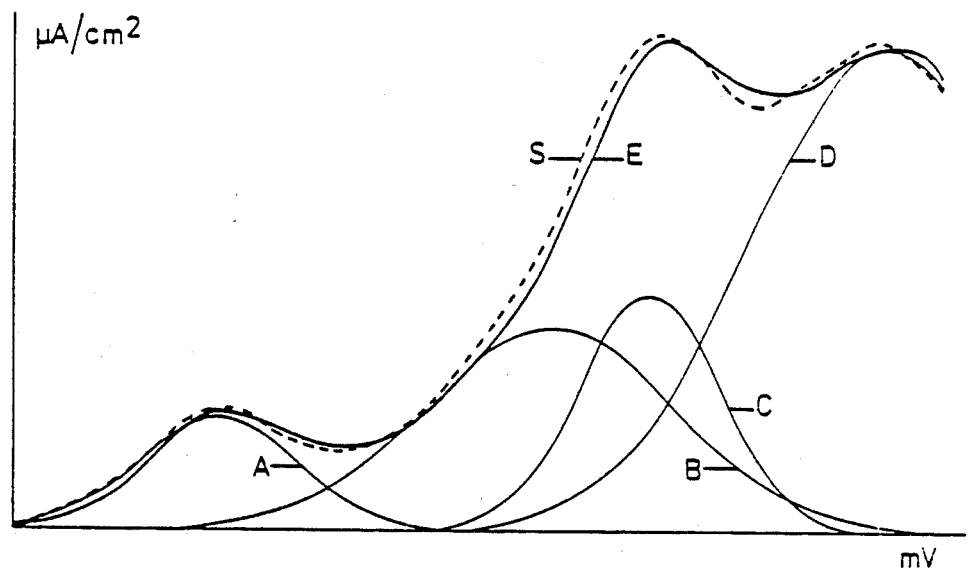

When the data required to plot such a graph has been obtained, this data can readily be resolved mathematically by a technique known per se to give an indication of the populations of the various ionic species in the molten glass. Such a resolution is shown graphically in FIG. 9. In FIG. 9, solid curve E represents the experimentally derived relationship of current density to voltage when scanning from zero to negative. This curve is resolved mathematically into four Gaussian distribution curves A to D, of which:

curve A is centred at −380 mV indicating the presence of sulphur in the state $S^{4+}$, Curve B is centred at −520 mV indicating the presence of iron ions, curve C is centred at −580 mV indicating the presence of sulphur in the state $S^{4+}$, and curve D is centred at −680 mV indicating the presence of sulphur in the state $S^{6+}$.

The sum of these curves A to D is shown in broken lines as curve S, and while this does not coincide exactly with the experimentally derived curve E, the closeness of the fit between them indicates that this method of resolution is quite acceptable for practical purposes, and the concentration of the particular element species can be derived with sufficient accuracy from the resolved curves A to D.

Figures 10A, 10B:
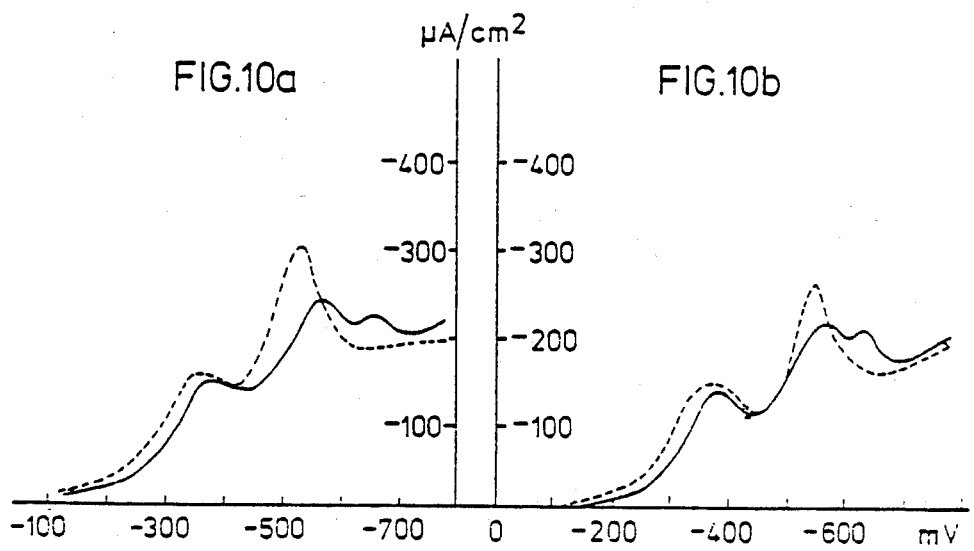

FIGS. 10a and 10b also show graphs of current density against voltage derived by a method according to the invention. The graphs of FIGS. 10a and 10b were obtained by measurements made in distribution channels of continuous tank furnaces containing compositions of glass having different concentrations of sulphur, that the FIG. 10a containing sulphur in an amount of 0.258% calculated as $SO_3$, and that of FIG. 10b containing sulphur in an amount of 0.233% calculated as $SO_3$. In those Figures, the solid line curves are derived by scanning with a potential which varies from zero to increasing negative values, and the broken line curves by scanning in the reverse direction, towards zero. It will be noted from these Figures that the solid curves each show three distinct peaks while the broken curves only show two.

However it must be emphasised that this invention does not depend on any explanation give for the phenomena which take place, nor in particular on any details of the ionic reactions which we understand to occur. Nevertheless, there do result peaks in the graphs of current density against voltage at certain applied potentials, and these are found to give an indication of the quantity particular element species and of their redox state.

Once the redox state of iron and/or sulphur in the glass has been measured, it is possible to modify that state in a controlled manner, for example by altering the fuel/air ratio fed to the furnace burners, or by altering the quantity of oxidizing and/or reducing agent incorporated in the batch fed to the furnace.

Another way of modifyig the redox state of the glass is to inject a gas into the melt. In fact air is often injected into the melt in a glass melting tank in order to give a stirring effect, and varying the rate at which such air is introduced will have an effect on the redox state of variable valency ions in the glass.

The measurements are conveniently made in the distribution or feeder channel of a glass melting furnace, though they may be made elsewhere.

It has been found that the monitored results are substantially independent of the yield of the glass melting furnace.

The apparatus used to effect the measurements illustrated in FIGS. 6 to 8 was a polarograph from Tacussel (France) model PRG 5, which comprises scanning potential and square wave pulse generators and a current density meter.

As an alternative, equipment comprising a calculator, a digital/analogue and analogue/digital converter, a potentiostat, a current measuring unit and a recorder could be used. In a particular example, a data processor, for example an "EXORSET" 165 (Trade Mark) from Motorola, controls a digital-to-analogue converter which feeds the required scanning potential with superimposed pulses to the electrodes immersed in molten glass. The current flowing between the electrodes is fed to an operational amplifier which in turn feeds an analogue-to-digital converter with a signal whose potential is proportional to the monitored current. The digital signal is then fed to the data processor and can be stored, for example on diskette. With a real time base, a suitable printer and suitable programming, a graph of the type shown in any of FIGS. 6 to 10 can be generated automatically as desired. Such apparatus was used to effect the measurements illustrated in FIGS. 9, 10a and 10b.

In some cases, it is useful not only to measure the redox state of one or more elements in the glass as described, but to couple this measurement with an analysis of the oxygen content (and of the acidity) of the molten glass. That can be evaluated by measuring the activity of oxygen using a potentiometric probe. Such a probe can be used to measure the partial pressure of oxygen dissolved in the molten glass, and may comprise two electrodes, a stabilised zirconia reference electrode, and an indicator electrode formed by a piece of platinum immersed in the glass. This gives complementary information on the redox state of the melt.

We claim:

1. A method of monitoring the redox state of at least one element in glass, comprising:

(a) immersing a working electrode and an auxiliary electrode in the glass while the glass is molten;

(b) applying a scanning potential to the working electrode, with a series of potential pulses being superimposed on the scanning potential; and (c) monitoring the resulting current between the electrodes to give an indication of the redox state of the at least one element in the glass.

2. A method according to claim 1, wherein said monitoring step is effected on molten glass having a temperature corresponding to a viscosity between $10^{5.2}$ and $10^{1.5}$ poises.

3. A method according to claim 2, wherein the temperature of the glass corresponds to a viscosity between $10^{3.3}$ and $10^{2.8}$ poises.

4. A method according to claim 1, wherein said scanning step includes varying the scanning potential linearly with time.

5. A method according to claim 1, wherein said scanning step includes scanning the scanning potential over a range which includes the range from 0 to +500 mV.

6. A method according to claim 1, wherein said scanning step includes scanning the scanning potential over a range which includes the range from 0 to −1000 mV.

7. A method according to claim 1, wherein said scanning step includes scanning the scanning potential to and fro in positive- and negative-going directions.

8. A method according to claim 1, wherein said monitoring step is effected on soda-lime glass and said scanning step includes scanning the scanning potential over a range which includes at least one of the following potentials: +120 mV, 0, −105 mV, −380 mV, −520 mV, −580 mV, −680 mV and −750 mV.

9. A method according to claim 1, wherein the superimposed pulses are uniform square wave pulses.

10. A method according to claim 1, wherein said monitoring step includes monitoring the difference between the current flowing immediately before the end of one of the potential pulses and the current flowing immediately before the start of that pulse.

11. A method according to claim 1, wherein the auxiliary electrode includes plates spaced apart from one another and said method further includes locating the working electrode between the plates of the auxiliary electrode, and wherein said immersing step includes immersing the electrodes in the glass so that such electrode plates define sides of a channel through which can flow natural or induced currents of molten glass.

12. A method of manufacturing glass from a composition containing at least one variable valency element and at least one of an oxidizing and reducing agent comprising:

(a) melting the composition to produce molten glass;

(b) monitoring the redox state of the at least one variable valency element in the molten glass by the monitoring method of claim 1; and (c) adjusting the quantity of the at least one of the oxidizing and reducing agents in dependence on the indication of the redox state of the at least one variable valency element as determined by said monitoring step.

13. A method of manufacturing glass from a composition containing at least one variable valency element, comprising:

(a) melting the composition to produce molten glass with the use of burners fed by a mixture of fuel and air;

(b) monitoring the redox state of the at least one variable valency element in the molten glass by the method according to claim 1; and (c) adjusting the mixture of fuel and air fed to the burners in dependence on the indication of the redox state of the at least one variable valency element as determined by said monitoring step.

14. A method of manufacturing glass from a composition containing at least one variable valency element, comprising:

(a) melting the composition to produce molten glass;

(b) monitoring the redox state of the at least one variable valency element in the molten glass by the method of claim 1; and (c) injecting gas into the melt at a rate which is adjusted in dependence on the indication of the redox state of the at least one variable valency element as determined by said monitoring step.

15. Apparatus for monitoring the redox state of elements in glass, comprising:

(a) a working electrode and an auxiliary electrode constructed for immersion in molten glass;

(b) means connected to said electrodes for applying a scanning potential to said working electrode and for superimposing potential pulses on the scanning potential; and (c) means operatively associated with said electrodes for monitoring resulting current flow between the electrodes.

16. Apparatus according to claim 15, wherein said electrodes are comprised of one of platinum and a platinum alloy.

17. Apparatus according to claim 15, wherein said auxiliary electrode is comprised of plates spaced apart from each other and said working electrode is located between said plates.

18. Appartus according to claim 15, wherein said working electrode is of substantially circular cross section.

19. Apparatus according to claim 15, wherein said working electrode comprises a stem and an enlarged working portion for immersion in the glass.

20. Apparatus according to claim 15, wherein said means for superimposing the potential pulses comprises a square wave generator.

21. Apparatus according to claim 15, wherein said means for monitoring current flow comprises a polarograph.

22. Apparatus according to claim 15, wherein said electrodes having connecting leads and further comprising a support means for mounting said electrodes, said support means including a conduit for housing said connecting leads and a cooling jacket operatively associated with said conduit for cooling said leads.

* * * * *